United States Patent [19]

Callahan et al.

[11] Patent Number: 4,658,015

[45] Date of Patent: Apr. 14, 1987

[54] POLYPEPTIDE INTERMEDIATES

[75] Inventors: James F. Callahan, Philadelphia; William F. Huffman, Malvern; Michael L. Moore, Media; Nelson C. Yim, Ambler, all of Pa.

[73] Assignee: SmithKline Beckman Corporation, Philadelphia, Pa.

[21] Appl. No.: 852,869

[22] Filed: Apr. 16, 1986

Related U.S. Application Data

[62] Division of Ser. No. 673,829, Nov. 21, 1984, Pat. No. 4,604,378.

[51] Int. Cl.$^4$ ............................ C07K 7/06; C07K 7/16
[52] U.S. Cl. .................................... 530/329; 530/315; 514/807
[58] Field of Search ................. 530/329, 315; 514/807

[56] References Cited

U.S. PATENT DOCUMENTS 4,491,577 1/1985 Manning et al. .

OTHER PUBLICATIONS

Journal of the American Chem. Soc. 94, (1972) 982-4.
Chem. Abstr. vol. 84, (1976) 122328.
Collect. Czechoslov. Chem. Commun., vol. 43, (1978) 511-522.
Chem. Abstr., vol. 81, (1974) 114962.
Chem. Abstr., vol. 84, (1976) 31421.
Chem. Abstr., vol. 93, (1980) 215771.
Proc. Natl. Acad. Sci. 76, pp. 3309-3313 (1979).
Biochem. and Biophys. Res. Commun. 49, (1972) 748-51.
Chem. Abstr., vol. 78, (1973) 72580.
Chem. Abstr., vol. 76, (1972) 55474.
Chem. Abstr., vol. 80, (1974) 108863.
Chem. Abstr., vol. 82, (1975) 26429.
Journal of the American Chem. Soc. 94, (1972) 5478-80.
J. Lowbridge et al., J. Med. Chem. 22 565 (1979).
M. Manning et al., J. Med. Chem. 20 1228 (1977).
J. Bankowski et al., J. Med. Chem. 21 350 (1978).
H. Schulz et al., J. Med. Chem. 9 647 (1966).
Derwent Abstract of European Patent No. 112,809-A.
M. Manning et al., J. Med. Chem. 25 (1982).
Peptides: Chemistry, Structure and Biology (Ann Arbor Sciences) 737 (1975).

*Primary Examiner*—Delbert R. Phillips
*Attorney, Agent, or Firm*—William H. Edgerton; Stuart R. Suter; Alan D. Lourie

[57] ABSTRACT

Certain vasopressin-like peptides, which have an acyclic unit at position 1 and which have an ω-amino- or guanidinoalkyl substituent attached to the cysteine in the 6-position of the ring, have $V_1$-vasopressin and oxytocin antagonist activity. A species of this series of new compounds is [1-desaminopenicillamine-2-(O-ethyl-D-tyrosine)-8-(1,4-diaminobutane)-9-desglycinamide]-vasopressin.

3 Claims, No Drawings

POLYPEPTIDE INTERMEDIATES

This is a division of application Ser. No. 673,829 filed Nov. 21, 1984, now U.S. Pat. No. 4,604,378.

This invention relates to certain basic cyclic peptides which are $V_1$-vasopressin and oxytocin antagonists. More specifically, the basic structure of these cyclic peptides has an acyclic β-mercaptopropionic acid at position 1 and five amino acid units cyclized into a 6-unit ring by means of a sulfur derived from the cysteine unit and a sulfur from the propionic acid unit. The ring has a distinguishing basic amino-alkyl or guanidinoalkyl tail which is attached via an amido linkage to the 6-cysteine unit of the ring, either directly or through another amino acid.

BACKGROUND OF THE INVENTION

A number of synthetic modifications of the vasopressin and oxytocin structures have been reported to give antagonistic activities. Such structures contain units which are derived from β-mercaptopropionic acids, for example, desamino-penicillamine or β-mercaptopropionic acid, substituted for the cysteine unit at position 1 of the structure of the natural product: J. Lowbridge et al., J. Med. Chem. 22 565 (1979); M. Manning et al., J. Med. Chem. 20 1228 (1977); K. Bankowski et al., J. Med. Chem. 21 350 (1978); H. Schulz et al., J. Med. Chem. 9 647 (1966). Ferring, A.B., European Patent No. 112,809-A discloses that certain Mpr[1] oxytocin derivatives have oxytocin antagonist activity.

Later studies by M. Manning et al., J. Med. Chem. 25 408 (1982) and Peptides: Chemistry, Structure and Biology (Ann Arbor Sciences) 737 (1975), demonstrated that no clearly consistent pattern of increasing or decreasing antagonist potency has emerged from research in this area but, in most of the series studied, the β,β-diethyl and β,β-cyclopentamethylene propionic acid units at position 1 were much more active than were the lower homologues, see column 1 on page 411 of the first Manning reference.

Ser. No. 535,000, a U.S. application which was earlier filed and is commonly assigned, but is now abandoned in favor of pending Ser. No. 645,127, discloses the preparation and $V_2$-antagonistic activity of certain vasopressin-like compounds having a 1-(β-mercapto-β,β-cycloalkylene)-propionic acid at position 1 and a diaminoalkyl group at position 7 or 8.

In the description herein and in the claims, the nomenclature common in the art of peptide and, more specifically, vasopressin chemistry is used. When no configuration is noted, the amino acid unit is in the L or naturally occuring form. The thio members of the β-mercaptopropionic acid (1) and cysteine (6) units are added for clarity in certain structural formulas.

Exemplary of the peptide art designations used herein are the following: dPen, β-mercapto-β,β-dimethylpropionic acid; Put, putrescine; Cad, cadaverine; Mpr, β-mercaptopropionic acid; Trp, tryptophan; Thr, threonine; OXT, oxytocin; Abu, α-aminobutyric acid; Chg, cyclohexylglycine; Cha, cyclohexylalanine, Pba, α-aminophenylbutyric acid; Gln, glutamine; Gly, glycine; Tyr, tyrosine; Phe, phenylalanine; Val, valine; Ile, isoleucine; Nle, norleucine; Leu, leucine; Ala, alanine; Lys, lysine; Asn, asparagine; Tos, tosylate; Sar, sarcosine; BHA, benzhydrylamine; DIEA, diisopropylethylamine; 4-MeBzl, 4-methylbenzyl; TFA, trifluoroacetic acid, DCC, dicyclohexylcarbodiimide; HBT, 1-hydroxybenzotriazole; ACM, acetamidomethyl; Mpa, generic β-mercaptopropionic acids of the present invention.

DESCRIPTION OF THE INVENTION

The basic $V_1$-antagonist compound of the invention are illustrated by the following structural formula:

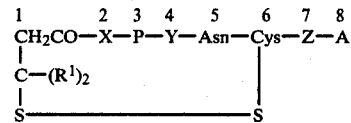

in which:

A is $-NR-(CH_2)_n-NR_2$ or

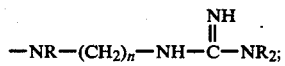

P is Phe, Ile, Phe(4'-Alk), Tyr or Tyr(Alk);

X is a D or L isomer of Val, Nva, Leu, Ile, Pba, Phe, Phe(4'-Alk), Trp, Nle, Cha, Abu, Met, Chg, Tyr or Tyr(Alk);

Y is Val, Ile, Abu, Ala, Chg, Gln, Lys, Cha, Thr, Nle, Phe, Leu or Gly;

Z is Gly, Sar a single bond or a D or L isomer of Pro, $\Delta^3$-Pro, Ala or N-MeAla;

$R^1$ is, in each instance, hydrogen or methyl;

n is an integer from 2-8 inclusive; and

R is, in each instance, hydrogen or methyl; or a pharmaceutically acceptable salt, complex or prodrug thereof.

"Alk" in formula I and hereafter represents a lower alkyl of 1-4 carbons which may be a substituent which is optionally attached either to a phenyl of an amino acid unit such as Phe at position 3 or to an oxygen substituent such as that of a tyrosine unit when the latter is present such as at position 2. Such alkyl substituents include methyl, ethyl, n-propyl, isopropyl or butyl, Preferably, Alk is methyl or ethyl. "Bzl" represents benzyl.

When the term, "vasopressin" or "VSP" is used, it means L-arginine vasopressin (AVP) unless otherwise modified. Certain antagonists with ring structures related to oxytocin (OXT) are also included in this invention.

In the compounds represented by formula I, those with structures which have dPen at position 1, an L unit at 2 and Pro at 7 are preferrred for selective $V_1$-antagonist activity. The latter activity has beneficial results in treating cardiovascular disorders which are susceptible to specific vasodilation.

The β-mercaptopropionic acid unit at position 1, Mpa[1], includes the unsubstituted, the β,β-dimethyl as well as the β-monomethyl congeners. The latter may be in the form of a separated optical isomer or a mixture of isomers.

A subgeneric group of compounds of this invention comprises compounds of formula I in which P is Phe, X is D-Tyr or D-Tyr(Alk); Y is Ile or Gln; each R is hydrogen and Z is Pro, D-Pro or a single bond.

Also included in this invention are salts and complexes of the compounds of this invention, especially the nontoxic, pharmaceutically acceptable salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of formula I have an additional strong basic group in their structures, therefore, their acid addition salt derivatives are easily prepared. Often, the end products are isolated as the acetate salts which are formed during purification.

The compounds of formula I are prepared by the following reaction:

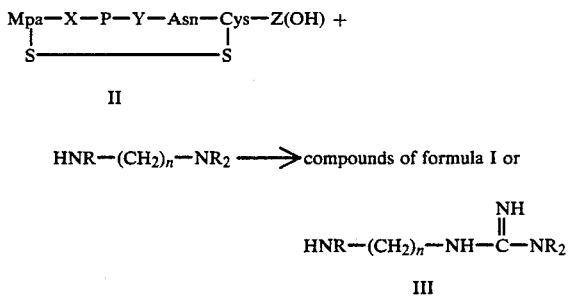

in which X, Z, Y, n, P, Mpa and R are as defined above. Mpa, of course, refers to the $\beta$-mercaptopropionic acid unit at position 1 of the structures of formula I. The compounds of formula II are important new intermediates and are part of this invention.

The dibasic compound (III) is used in the chemical reaction in a protected form at one of the two basic centers, if necessary. For example, a compound whose structure has an amino (—NH$_2$) or a secondary amino (—NHR) is reacted conveniently as the Boc derivative. When guanidino is present in its structure, reactant III is reacted as a tosylate derivative as known to the art. Other amino protecting groups, which are known to the art, may be used alternatively.

The reaction of the starting material carboxylic acid (II) with the base (III), protected if necessary, is carried out using any amide forming reaction common in the peptide art. For example, substantially equimolar quantities of the two starting materials are reacted in the presence of a carbodiimide, such as dicyclohexylcarbodiimide, plus 1-hydroxybenzotriazole in an organic solvent at room temperature until the reaction is complete.

The protective groups are then, if present, removed by methods known to the art such as reaction in the presence of trifluoromethanesulfonic acid and trifluoroacetic acid/anisole at room temperature for the tosylate (guanidine) or reaction using trifluoroacetic acid in the cold for the Boc (amine) protecting groups.

The guanidino congeners are also prepared from their amino-containing counterparts directly by reaction of the latter with a compound such as an O-methylisourea. The reaction is usually carried out at a moderately basic pH, in an aqueous solution in the cold, until the reaction is complete.

As stated above, the starting materials (II) for the reaction described above are part of this invention. They are new intermediate compounds which also have VSP antagonist activity, even though at a much higher dose than do the compounds of formula I. These compounds are prepared, as are the end products of formula I for an alternative route, by oxidation of the following linear peptide;

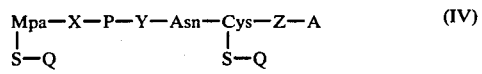

in which X, Z, Y, Mpa and P are as defined above, especially for formula I, and A is OH or as defined for formula I above. The mercapto groups are members of the Mpa and Cys units. Each Q is hydrogen or a displaceable group such as acetamidomethyl (ACM). The dithiol of formula IV is, optionally, also oxidized in the form of an amide derivative of the unit at position 6 or 7. For example, the amide may be —NHR, —NH$_2$ or an A-containing amide derivative. The latter amide, as defined for structure I, gives the end products directly after cyclization and after removal of any protective groups.

Said oxidation is carried out using an excess of an alkali metal ferricyanide, such as potassium or sodium ferricyanide, with the linear intermediate IV. A suitable unreactive solvent, preferably an aqueous-miscible solvent at a neutral pH, about 7-7.5, is used. Reaction is carried out at ambient temperature or lower until the reaction is substantially complete. Preferably, the concentrations of the linear peptide dimercaptan and the oxidizing agent are low, say 0.01-0.1 molar concentration of oxidizing agent in several liters of aqueous solution to cyclize 1-5 grams of dimercaptan.

Other mild oxidation agents having an oxidation potential roughly equivalent to ferricyanide may also be used for the ring closure reaction. Oxygen passage through the reaction solution for several days or iodine in methanol are such alternatives. Cyclization, also, occurs when a displaceable, thiol-protective group such as that at the mercaptan group of the Mpa unit is displaced intramolecularly.

An especially useful thio protective group is acetamidomethyl (ACM). Iodine/alcohol is used for direct, one-pot cyclization of the bis-ACM-S-linear peptide. Of course, one skilled in the art will recognize that certain cyclization methods are not appropriate if an interfering reaction site is present in the structure of the starting material of formula IV. The linear mercaptan starting material may have protective groups, which are common to the art, temporarily present at the various linear units.

The intermediates of formula IV are conveniently prepared using either solid-phase or liquid methods of peptide synthesis.

The peptide chain of the linear peptides is usually built up, stepwise, proceeding from the Z unit and working toward the Mpa unit. Each unit is properly protected as known in the peptide art and as described below. The sequence of step-reactions is conveniently carried out in a Beckman 990B peptide synthesizer without isolation of each intermediate peptide. The details of the procedure are in the working examples presented hereinafter.

The various amino acids (AA), which are consecutively added to the resin supported chain, are protected as known to the art. For example, the Boc protecting group is used for an amino group, especially at the $\alpha$-position of an amino acid unit; an optionally substituted benzyl or an acetamidomethyl, for the mercapto groups at the Mpa and Cys units; and an optionally substituted carbobenzoxy (Z) for the hydroxy of the Tyr units. The protective groups should, most conveniently, be those which are easily removed, that is, using acid treatment for the Boc group, sodium-liquid ammonia or modified catalytic hydrogenation for the benzyl or carbobenzoxy groups.

The resin-supported peptide is treated with an excess of anhydrous hydrogen fluoride with an appropriate scavenger compound, such as anisole, to give the linear peptide intermediate of formula IV in good yield.

The compounds of this invention have potent $V_1-V_2$ vasopressin or oxytocin antagonist activity with a shift toward the $V_1$-receptors in the $V_1-V_2$ biological spectrum. Vasopressin is primarily known to contribute to the anti-diuretic mechanism of action with the kidney.

When the action of these compounds antagonizes that of the natural anti-diuretic hormone (ADH), the body excretes water due to an increased permeability of the terminal portions of the renal tubule. This mechanism of action is at the vasopressin receptors [$V_2$-receptors] located on the plasma membrane of certain renal epithelial cells.

Any patient suffering from the syndrome of inappropriate antidiuretic hormone secretion (SIADH) or from an undesirable edematous condition is a target for the claimed compounds when they act as $V_2$-antagonists. Examples of clinical conditions indicated for the compounds of this invention include hypertension, hepatic cirrhosis, congestive heart failure or a component of any traumatic condition resulting from serious injury or disease. The compounds have weak $V_2$-antagonist activity compared with other similar prior art compounds.

The second group of vasopressin receptors, which are more important targets of this invention, are those affecting the smooth muscle tissues of the blood vessels or of the uterus. Vasopressin or oxytocin are natural stimulants of these effectors which result in pressor effects on the cardiovascular system and stimulation of the uterus, respectively. These receptors are jointly called $V_1$ receptors for the over-all purpose of this disclosure since the compounds here disclosed have both activities.

More specifically, vasopressin $V_1$-antagonists will counter the pressor activity in vascular beds induced by naturally occurring vasopressin. They are, therefore, specific vasodilators. The activity of $V_1$-antagonists will be manifested in treating various abnormal cardiovascular conditions such as hypertension, shock, coronary or other ischemias. They are optionally used in conjunction with ACE inhibitors, $\beta$-blockers or $\alpha$-blockers.

The compounds of the present invention are, therefore, antagonists at $V_1$ receptor sites as well. In fact, the $V_1-V_2$ ratio of activities of the compounds of this invention is shifted toward greater relative $V_1$ antagonism. Especially active $V_1$ antagonists are those of formula I in which X is a L-amino acid residue and Y is a glutamine residue. These compounds, therefore, have potent selective vasodilation activity as described in more detail above.

The compounds of formula I which have amino acid units, other than at position 1, which resemble those of oxytocin especially have potent anti-oxytocic activity. Therefore, such compounds are particularly useful to relax uterine tissues. The activity is opposite that of oxytocin. Exemplary of such compounds are the basic compounds of formula I in which Z is proline or a single bond; X is a D-O-alkyltyrosine; P is phenylalanine or isoleucine; and Y is glutamine or threonine. Generally, the compounds of this invention have more enhanced anti-oxytocic activity than would have been expected.

The compounds of this invention, therefore, are mainly used to induce selective vasodilating or antioxytocic activity, but, also, to a lesser extent to treat edema, in patients in need of such antagonist treatment by administering the compounds internally, particularly parenterally or by insufflation, to human or animal patients in need of such treatment. A nontoxic but effective quantity of the chosen compound is preferably combined with a pharmaceutical carrier. Dosage units of the active ingredient are selected from the range 10 $\mu$g to 10 mg/kg, preferably 15 $\mu$g to 1 mg/kg, based on a 70 kg patient. The dosage units are administered from 1 to 5 times daily or by continuous intravenous drip.

The pharmaceutical composition of this invention, which contains an active ingredient of formula I, comprises a dosage unit as described above dissolved or suspended in a standard liquid carrier, such as isotonic saline, contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, emulsions or aerosols. Quantities of the active ingredient in nasal products are from 3–7 times greater than those in parenteral products.

Antagonistic activity at the $V_1$-vasopressin receptors is determined in a protocol which measures the reversal of the vasopressin-induced contraction of rat thoracic aorta tissue. This is expressed as $K_B$ (nM) in the table below. Such anti-pressor activity is confirmed in a similar in vitro protocol using binding to the plasma membranes of rat liver. $V_2$-vasopressin antagonism is determined as receptor binding ability measured by inhibition of 3H-LVP binding ($K_B$ as nM), by inhibition of adenylate cyclase activation by vasopressin in the medullary tissue of hog kidneys (Ki as nM) or in vivo in the hydropenic rat protocol (ED$_{300}$ $\mu$g/kg). These procedures are described in the literature: F. Stassen et al., J. Pharmacology and Experimental Therapeutics, 223 50 (1982); F. Stassen et al., 1st International Conference on Diuretics, Miami, Fla., March (1984). Antagonistic activity at oxytocin receptors is determined in the isolated rat uterus protocol: W. Sawyer, et al., Endocrinology 106 81 (1979); P. Melin, et al., J. of Endocrinology 88 173 (1981).

TABLE 1

Representative Antagonist Activity

| Compound | Pig $V_2$[a] $K_B$ (nM) | Rat $V_1$[b] $K_B$ (nM) | Rat $V_1$[c] $K_B$ (nM) | Rat OXT[d] $K_B$ (nM) | Rat $V_2$[e] ED$_{300}$ ($\mu$g/kg) |
|---|---|---|---|---|---|
| A | 8600 | — | 1.21 | 5.91 | — |
| B | 70 | 2.9 | — | — | — |
| C | 5700 | — | — | 1.6 | >591 |
| D | 4100 | — | — | 17.7 | >5018 |

TABLE 1-continued

Representative Antagonist Activity

| Compound | Pig V$_2$[a] K$_B$(nM) | Rat V$_1$[b] K$_B$(nM) | Rat V$_1$[c] K$_B$(nM) | Rat OXT[d] K$_B$(nM) | Rat V$_2$[e] ED$_{300}$ (μg/kg) |
|---|---|---|---|---|---|
| E | 1600 | — | — | 11.4 | ~2037 |

[a]Medullary pig kidney tissue,
[b]Rat liver membrane,
[c]Rat aortic ring tissue,
[d]Rat uterus,
[e]Hydropenic rat.

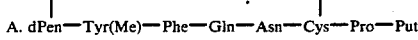

A. dPen—Tyr(Me)—Phe—Gln—Asn—Cys—Pro—Put

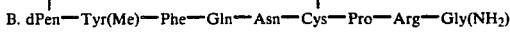

B. dPen—Tyr(Me)—Phe—Gln—Asn—Cys—Pro—Arg—Gly(NH$_2$)

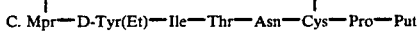

C. Mpr—D-Tyr(Et)—Ile—Thr—Asn—Cys—Pro—Put

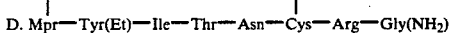

D. Mpr—Tyr(Et)—Ile—Thr—Asn—Cys—Arg—Gly(NH$_2$)

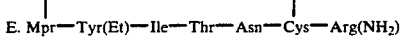

E. Mpr—Tyr(Et)—Ile—Thr—Asn—Cys—Arg(NH$_2$)

The data in Table 1 demonstrate a shift to potent V$_1$ and enhanced OXT antagonistic activity from the antagonism demonstrated by representative des-Pro or tripeptide tailed compounds. Weak V$_2$-antagonism is, however, still demonstrated by the compounds of this invention.

The following examples are designed to teach the preparation and use of this invention. All temperatures are Centigrade.

EXAMPLE 1

Procedure for the general synthesis of the cyclic acid interxediates (II):

Boc-Pro-Merrifield resin was made by coupling Boc-Pro to Merrifield resin using the cesium salt method to give Boc-Pro-OCH$_2$C$_6$H$_4$-resin which was used as the starting material for the synthesis. The synthesis was carried out on the Beckman 990B peptide synthesizer using the following protocol. Three equivalents of the amino acids were dissolved in their appropriate solvents [the Boc derivatives of 4-MeBzl-Cys, Val, Phe and 4-MeBzl-Mpa in methylene chloride, Asn in dimethylformamide, D-Tyr(Et) or BrZ-D-Tyr in 1:1 methylene chloride/dimethylformamide] and were coupled using an equimolar amount of dicyclohexylcarbodiimide (DCC) and 1-hydroxybenzotriazole (HBT) except for the coupling of 4-MeBzl-Mpa where 1.0 equivalent of dimethylaminopyridine was used as catalyst. The extent of coupling was determined by qualitative ninhydrin analyses of each aliquot sample and couplings were repeated when necessary. The Boc groups were removed using 1:1 trifluoroacetic acid/methylene chloride and, after washing, the free amine was generated using 5% diisopropylethylamine/methylene chloride. The sequence of the peptide was checked using solid phase sequencing before the coupling of the 4-MeBzl-Mpa and its homogeneity confirmed. After the final coupling, the peptide was dried and used as such in the cyclization.

The 1-Mpa peptide resin (0.5 mmol) with 3 ml of anisole was stirred for 60 minutes at 0° (ice bath) in 25 ml of anhydrous liquid hydrogen fluoride (HF). The HF was then removed under reduced pressure at 0°. The residue was washed with ethyl ether (4×20 ml, discarded) and the peptide eluted with dimethylformamide (3×10 ml), 20% acetic acid (3×10 ml) and 0.3N ammonium hydroxide (3×10 ml).

The filtrate was added to 2 l of degassed water and the pH adjusted to 7.1 with conc. ammonium hydroxide. A 0.01M solution of potassium ferricyanide was then added dropwise with stirring until a faint yellow color persists (41 ml).

The resulted solution was then passed through a flash column (5 cm×15 cm) of a packing of octadecylsilane (C$_{18}$) bonded to silica gel (~40 μm). The column was, then, washed with 350 ml of water and the peptide eluted with 500 ml of 1:1 acetonitrile/water (0.1% trifluoroacetic acid) in 20 ml fractions. The residue from the product containing eluants was dissolved in conc. acetic acid, diluted with water and lyophilized to give the cyclized acid intermediate, which was used without further purification for the synthesis of the basic tail modified peptides.

A. Identification of [1-desaminopenicillamine-2-(O-methyl)-L-tyrosine-8-desarginine-9-desglycinamide]-vasopressin.

A total of 183 mg of pure titled 7-proline intermediate was obtained from a 1 mmole run as described above. Purification was by: 1. C$_{18}$-flash column chromatography, 2. CCD, and 3. gel filtration.

Analysis: C$_4$H$_{56}$N$_9$O$_{10}$S$_2$ (molecular weight, 898).

1. Fast atom bombardment (FAB) mass spectrum: 899 (M+H)$^+$ (positive ion observed); 897 (M−H)$^-$ (negative ion observed).

2. Amino acid analysis (AAA): Asp, 1.03; Pro, 0.97; Phe, 0.95; Glu, 1.00; Tyr, 0.79; Cys, —; peptide content 90%.

3. High pressure liquid chromatography (HPLC): 5μ, C$_{18}$ column:

Solvent A: 0.1% trifluoroacetic acid in water.
Solvent B: 0.1% trifluoroacetic acid in acetonitrile.
From 20% B to 50% B in 30 minutes, eluted at 33.01 min.

B. Identification of [1-mercaptopropionic acid-2-(O-ethyl)-D-tyrosine-3-isoleucine-4-threonine-8-desarginine-9-desglycinamide]-vasopressin.

A total of 290 mg of pure titled heptapeptide intermediate was obtained from a 1 mmole run as described above. Purification was as described.

Analysis: C$_{36}$H$_{53}$N$_7$O$_{11}$S$_2$ (molecular weight, 823).

1. FAB-MS: 824 (positive ion observed) (M+H)$^+$; 822 (negative ion observed) (M−H)$^-$.

2. AAA: Asp, 1,00; Pro, 1.05; Ile, 0.91; Thr, 0.97, Cys, 0.30; Tyr, 0.91; peptide content, 95%.

3. HPLC, 5μ, C$_{18}$ column:
Solvent A: 0.1% TFA in H$_2$O.
Solvent B: 0.1% TFA in CH$_3$CN.
Linear gradient from 20% B to 50 B in 30 minutes, eluted at 27.6 min.

EXAMPLE 2

1,5-Diaminopentane (14.0 ml, 120 mmol) was dissolved in tert.-butanol (70 ml) and was treated dropwise over a period of 10 minutes with di-tert-butyl dicarbonate (9.2 ml, 40 mmol). After the addition had been completed, the reaction mixture was stirred at room temperature for 16.5 hours. The reaction mixture was then treated with 1N sodium hydroxide solution (aq) (90 ml), stirred for 1 hour and finally extracted with chloroform. The chloroform extracts were dried (MgSO$_4$) and concentrated under vacuum. The residue was dissolved in water, made acidic (pH=2) by the dropwise addition of 3N hydrochloric acid at 0° and was washed with ether to remove the diprotected diamine. The aqueous portion was made basic (pH 10) with 5% sodium carbonate solution and was extracted with ethyl acetate to give 1.6 g (20%) of mono-Boc-1,5-diaminopentane. The structure was confirmed by 'H NMR and CI-MS. The putrescine and other mono-Boc derivatives are prepared similarly.

To a solution of the proline intermediate from Example 1A, (40 mg, 0.044 mmol) and mono-Boc-1,4-diaminobutane (40 mg, 0.212 mmol) in dimethylformamide (2 ml), dicyclohexylcarbodiimde (14.0 mg, 0.07 mmol) and 1-hydroxybenzotriazole hydrate (9.0 mg, 0.07 mmol) were added. The reaction mixture was stirred at room temperature for 90 hours. The dimethylformamide was, then, removed under vacuum. The residue was treated with trifluoroacetic acid (6 ml) at room temperature for 2 hours. After this time, the trifluoroacetic acid was removed under vacuum and the residue in 1% acetic acid was passed over a BioRex 70 ($H^+$) ion exchange column. The basic products were washed off the ion exchange column with pyridine buffer ($H_2O$/pyridine/HOAc, 66:30:4) and evaporated. Subsequent purification by prep HPLC (5 $\mu$ Ultrasphere ODS) and gel filtration chromatography (G-15) gave 11.7 mg of pure [1-desaminopenicillamine-2-(O-methyl-L-tyrosine-8-(1,4-diaminobutane)-9-desglycinamide]-vasopressin. The structure of the product was confirmed by FAB-MS [$(M+H)^+ = 969$, $(M-H)^- = 967$]. The purity was confirmed by HPLC (5$\mu$ Ultrasphere ODS, 4.6×250 mm) $H_2O$/$CH_3CN$/0.1% TFA (70:30:0.1), eluted at 11.1 min. gradient, (80:20 to 50:50) $H_2O$/acetonitrile with 0.1% TFA, eluted at 16.0 min.

EXAMPLE 3

Guanidation of mono-Boc-1,4-diaminobutane:
Mono-boc-1,4-diaminobutane (1.25 g, 6.6 mmol), prepared from putrescine as in Example 2, in dioxane (2 ml) and water (6.5 ml) was treated with O-methylisourea hydrogen sulfate (1.25 g, 7.26 mmol) and 2N sodium hydroxide (aq) (3.75 ml) at room temperature. The resulting solution was stirred for 6 days. The solvent was removed under reduced pressure and the residue made basic (pH=12) by the addition of 2N sodium hydroxide. The residue was again evaporated, taken up in ethyl acetate, filtered and evaporated. The crude guanidine was dried by evaporation from toluene and used without further purification.

The crude guanidine (410 mg, 1.78 mmol) in 2N sodium hydroxide (aq) (2 ml) and water (2 ml) was treated at room temperature with p-toluenesulfonyl chloride (340 mg, 1.78 mmol) for 18 hours. The pH was adjusted to 8 with 5% sodium carbonate solution. The mixture was extracted with ethyl acetate to give, upon evaporation, 437 mg of crude product. Purification by flash chromatography (3×15 cm silica bed, 80% ethyl acetate/hexane) gave 265 mg (39%) of the desired tosylated product whose identity was confirmed by 'H NMR and CI-mass spectroscopy.

The Boc-tosyl-guanidino diamine (108 mg, 0.281 mmol) in methylene chloride (1 ml) was treated with trifluoroacetic acid (1 ml) at 0° for 40 minutes. The reaction was evaporated under vacuum, the residue's pH adjusted to 8 with 5% sodium carbonate solution and evaporated to dryness. The residue was taken up into ethyl acetate, filtered and evaporated. The crude des-Boc product was dried by evaporation from toluene to give 66 mg (82%). Identify was confirmed by 'H NMR and used without further purification.

[1-desaminopenicillamine-2-L-(O-methyl)-tyrosine-8-desarginine-9-desglycinamide]-vasopressin (35 mg, 0.039 mmol), prepared as in Example 1A, in dimethylformamide (0.5 ml) is treated at room temperature with the tosyl guanidino amine (33 mg, 0.114 mmol), DCC (12 mg, 0.057 mmol) and HBT (8 mg, 0.057 mmol). The mixture is stirred for 43 hours. The solvent is removed at reduced pressure and the residue is dissolved in trifluoroacetic acid (2 ml), then treated at room temperature with trifluoromethanesulfonic acid (150 $\mu$l, 1.7 mmol) and anisole (37 $\mu$l) with stirring for 2 hours. The reaction mixture is evaporated to dryness, dissolved in 10% acetic acid, filtered and passed through a BioRex-70 column. The crude guanidino peptide is eluted off the column with pyridine buffer (pyridine/water/acetic acid, 30:66:4), evaporated and the residue purified by preparative HPLC (5$\mu$, ODS, $H_2O$/$CH_3CN$/TFA 60:40:0.1) to give [1-desaminopenicillamine-2-L-(O-ethyl)-tyrosine-8-(1-amino-4-guanidinobutane)superfluous-9-desglycinamide]-vasopressin.

EXAMPLE 4

A solution of 40 mg (0.044 mmol) of the Pro acid intermediate, prepared as in Example 1A, and mono-Boc-1,5-diaminopentane (26 mg, 0.129 mmol) in dimethylformamide (900 $\mu$l) is treated with dicyclohexylcarbodiimide (13 mg, 0.065 mmol) and 1-hydroxybenzotriazole hydrate (9 mg, 0.065 mmol) with stirring at room temperature for 43 hours. The dimethylformamide is, then, removed under vacuum. The residue is treated with trifluoroacetic acid at 0° for 1 hour. After this time, the trifluoroacetic acid is removed under vacuum and the residue in 1% acetic acid is passed through a BioRex 70 ($H^+$) ion exchange column. The basic products are washed off the column with pyridine buffer ($H_2O$)/pyridine/acetic acid, 66:30:4) and evaporated. Final purification by prep HPLC (5$\mu$ Ultrasphere ODS) gave pure [1-desaminopenicillamine-2-(O-methyl-L-tyrosine)-8-(1,5-diaminopentane-9-desglycinamide]-vasopressin.

EXAMPLE 5

A solution of 80 mg (0.097 mmol) of the proline acid of Example 1B and mono-t-Boc-1,4-diaminobutane (63 mg, 0.335 mmol) in dimethylformamide (3 ml was treated with dicyclohexylcarbodiimide (30 mg, 0.146 mmol) and 1-hydroxybenzotriazole hydrate (39 mg, 0.291 mmol), then stirred at room temperature for 48 hours. The dimethylformamide was removed under vacuum. The residue was treated with trifluoroacetic acid (5 ml) at room temperature for 2 hours. The trifluoroacetic acid was removed under vacuum and the residue was passed through a BioRex 70 ($H^+$) ion exchange column. The basic products were washed off the ion exchange column with pyridine buffer ($H_2O$/pyridine/acetic acid, 66:30:4) and evaporated to give [1-B-mercaptopropionic acid)-2-(O-ethyl-D-tyrosine)-3-isoleucine-4-threonine-8-(1,4-diaminobutane)-9-desglycinamide]-vasopressin. Final purification by prep HPLC (5$\mu$ Ultrasphere ODS) gave 12 mg of pure product. The structure of the product was confirmed by FAB-MS [$(M+H)^+ = 894$, $(M-H)^- = 892$]. The purity was confirmed by HPLC (5$\mu$ Ultrasphere ODS, 4.6×250 mm; water/acetonitrile/TFA (70:30:0.1), eluted at 15.4 min; gradient 80:20 to 50:50, $H_2O$/$CH_3CN$/0.1% TFA; eluted at 18.2 min).

Substituting α-aminobutyric acid in the chemical procedure above gives [1-(β-mercaptopropionic acid)-2-(α-aminobutyric acid)-3-isoleucine-4-threonine-8-(1,4-diaminobutane)-9-desglycinamide]-vasopressin. Using similarly protected β-(S-methylbenzylmercapto)-β-methylpropionic acid in place of Mpr in the method of Examples 1 and 5 gives [1-(β-mercapto-β-methylpropionic acid)-2-(O-ethyl-D-tyrosine)-3-isoleucine-4-threonine-8-(1,4-diaminobutane)-9-desglycinamide]-vasopressin. Substituting N,N-dimethylethylenediamine for Boc-putrescine above gives [1-(β-mercaptopropionic acid)-2-(O-ethyl-D-tyrosine)-3-isoleucine-4-threonine-8-(2-(N,N-dimethylamino)-1-amino-ethane)-9-desglycinamide]-vasopressin. Substituting monoformylcadaverine above followed by formic acid reduction of the formyl group gives the N-methylcadaverine derivative.

EXAMPLE 6

Synthesis of [1-desaminopenicillamine-2-(O-methyl)-tyrosine-7-desproline-8-desarginine-9-desglycinamide]-vasopressin.

The titled compound is prepared by means of solid phase as described in Example 1 but using Boc-Cys-Merrifield resin as starting material which is subsequently coupled with the appropriate Boc-amino acids sequentially, followed by hydrogen fluoride deprotection, cleavage from the resin concurrently and, then, oxidative cyclization and purification are carried out as described in Example 1.

EXAMPLE 7

A solution of 0.043 mmoles of the cysteine acid, prepared as in Example 6, and mono-t-Boc-1,5-diaminopentane (26 mg, 0.129 mmol) in dimethylformamide (1 ml) is treated with dicyclohexylcarbodiimide (13 mg, 0.065 mmol) and 1-hydroxybenzotriazole hydrate (9 mg, 0.065 mmol) and is stirred at room temperature for 48 hours. The dimethylformamide is then removed under vacuum. The residue is treated with trifluoroacetic acid (5 ml) at room temperature for 3 hours. After this time, the trifluoroacetic acid is removed under vacuum and the residue therefrom dissolved in 10% acetic acid, then passed through a BioRex 70 (H+) ion exchange column. The basic products are washed off the ion exchange column with pyridine buffer (water/pyridine/acetic acid, 66:30:4) and evaporated to dryness to give [1-β-desaminopenicillamine-2-(O-methyl)-tyrosine-7-(1,5-diaminopentane)-8-desarginine-9-desglycinamide]-vasopressin.

EXAMPLE 8

Diaminoheptane (13.0 g, 100 mmol) was dissolved in 100 ml of methylene chloride. To this was added 8.72 g of di-t-butyldicarbonate (40 mmol) in 10 ml of methylene chloride over one hour. After stirring at room temperature overnight, a white precipitate formed which was collected by filtration. It was dissolved in 1N ammonium hydroxide and extracted with ethyl acetate. The ethyl acetate was washed with water and evaporated to dryness. The residue was dissolved in 1N sodium bisulfate, extracted with ethyl acetate and then made basic (pH 8-9) with ammonium hydroxide. This solution was extracted with ethyl acetate. The ethyl acetate was dried over magnesium sulfate and evaporated to dryness, yielding a pale yellow oil which solidified upon standing. The solid was triturated with hexane, collected by filtration and air-dried, yielding 350 mg (2%), mp 55-58, FAB-MS and proton NMR consistent with the structure of Boc-diaminoheptane.

The Pro-OH peptide of Example 1A (25 mg, 0.028 mmol) is dissolved in dimethyl formamide (5 ml). To this is added 18 mg Boc-diaminoheptane (31 mg, 0.135 mmol), HBT (0.135 mmol) and di-isopropylcarbodiimide (21 μl, 0.135 mmol). After stirring at room temperature overnight, the solvent is removed under vacuum. The residue is dissolved in chloroform which solution is washed with 1N sodium bisulfate followed by saturated brine and, then, evaporated to dryness several times from chloroform. The residue is dissolved in 4N HCl/dioxane and stirred at room temperature for 30 minutes. After evaporation of solvent, the residue is evaporated several times from chloroform, dissolved in water, adjusted to pH 3.5 with glacial acetic acid and applied to BioRex 70 column (H+). The column is washed with water and then eluted with pyridine acetate buffer (30% pyridine, 6% acetic acid). The buffer is evaporated to dryness and the residue lyophilized out of water. The peptide, [1-(β-desaminopenicillamine)-2-(O-methyl-tyrosine)-8-(1,7-diaminoheptane)-9-desglycinamide]-vasopressin, is purified by gel filtration chromatography in 1% acetic acid followed by preparative HPLC.

EXAMPLE 9

Procedure for solid phase synthesis of the basic end products of formula I:

Boc-S-(p-methylbenzyl)-L-cysteine is condensed with carbobenzoxycadaverine in methylene chloride using DCC/HOBT. The Boc is removed with 4N HCl/dioxane and the HCl salt is neutralized with triethylamine. The S-(p-methylbenzyl)-L-cysteinyl-carbobenzoxycadaverine is, then, condensed with fluorenylmethyloxycarbonyl-β-t-butyl-L-aspartic acid in DMF using DCC/HBT. The t-butyl ester is removed with 50% TFA/methylene chloride and the resulting Fmoc-Asp-Cys(MeBzl)-Cad-Z is coupled to benzhydrylamine resin using DCC/DAP. After removal of the Fmoc group with piperidine, the peptide is elongated according to the standard solid phase procedure as in Example 1. Treatment of the peptidyl resin with anhydrous liquid HF at 0 degrees affords the completely deprotected 7-(1,5-diaminopentane)-hexapeptide (IV), which is then oxidized to the cyclic disulfide end product with potassium ferricyanide in dilute aqueous solution as exemplified previously.

EXAMPLE 10

Substituting the appropriate protected amino acids in the above synthetic sequences gives the respective cysteine or proline acids, the basic peptide end products or a salt thereof as follows:

a. [1-desaminopenicillamine-2-(O-ethyl-D-tyrosine)-3-(4'-methylphenylalanine)-7-D-proline-8-(1,5-diaminopentane)-9-desglycinamide]-vasopressin sulfate;

b. [1-mercaptopropionic acid-2-(O-ethyl-D-tyrosine)-4-(α-aminobutyric acid)-7-(N-methyl-alanine)-8-(1,6-diaminoheptane)-9-desglycinamide]-vasopressin;

c. [1-(β-mercaptopropionic acid)-2-valine-4-cyclohexylglycine-7-sarcosine-8-(1,5-diaminoheptane)-9-desglycinamide]-vasopressin hydrochloride;

d. [1-(β-mercaptopropionic acid)-4-glutamine-8-(1,5-diaminopentane)-9-desglycinamide]-vasopressin;

e. [1-desaminopenicillamine-2-phenylalanine-7-(1-amino-5-guanidinopentane)-8-desarginine-9-desglycinamide-vasopressin;

f. [1-desaminopenicillamine-2-D-α-aminophenylbutyric acid-4-isoleucine-7-D-proline-8-(1-amino-4-N-methylaminobutane)-9-desglycinamide]-vasopressin;

g. [1-desaminopenicillamine-2-tryptophan-4-glutamine-7-(1-methylamino-5-N-propylaminopentane)-8-desarginine-9-desglycinamide]-vasopressin.

EXAMPLE 11

Parenteral Dosage Unit Compositions:

A preparation which contains 0.10 mg of the heptapeptide of Examples 2 or 5 as a sterile dry powder for parenteral injection is prepared as follows: 0.1 mg of peptide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from pressor effects susceptible to anti-ADH mechanism of action. The injection is repeated as necessary, from 1–5 times daily, or in continuous i.v. drip injection.

Nasal Dosage Unit Compositions:

2.5 Mg of a finely ground heptapeptide of this invention, such as the product of Example 4, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a cardiovascular subject from 1–6 times a day.

What is claimed is:

1. A polypeptide compound having the formula:

$$\begin{array}{c} CH_2CO-X-P-Y-Asn-Cys-Z(OH) \\ | \qquad\qquad\qquad\qquad\qquad\qquad\qquad | \\ C-(R^1)_2 \\ | \\ S\rule{3cm}{0.4pt}S \end{array}$$

in which:

P is Phe, Ile, Phe(4'-Alk), Tyr or Tyr(Alk);

X is a D or L isomer of Val, Nva, Leu, Ile, Pba, Phe, Phe(4'-Alk), Trp, Nle, Cha, Abu, Met, Chg, Tyr or Tyr(Alk);

Y is Val, Ile, Abu, Ala, Chg, Gln, Lys, Cha, Thr, Nle, Phe, Leu or Gly;

Z is Gly, Sar, a single bond or a D or L isomer of Pro, $\Delta^3$-Pro, Ala or N-Me-Ala; and $R^1$ is methyl; or an acceptable salt thereof.

2. The compound of claim 1 in which Z is Pro.

3. The compound of claim 1 in which Z is a single bond.

* * * * *